(12) United States Patent
Kuhn et al.

(10) Patent No.: US 10,518,084 B2
(45) Date of Patent: Dec. 31, 2019

(54) FIXATION FOR IMPLANTABLE MEDICAL DEVICES

(71) Applicant: Medtronic, Inc., Minneapolis, MN (US)

(72) Inventors: Jonathan L. Kuhn, Ham Lake, MN (US); Michael P. Campbell, Blaine, MN (US); Vladimir Grubac, Brooklyn Park, MN (US); Kenneth D. Rys, Minneapolis, MN (US); Richard W. Swenson, Edina, MN (US); Charles L. Wilson, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/128,270

(22) Filed: Sep. 11, 2018

(65) Prior Publication Data

US 2019/0009078 A1    Jan. 10, 2019

Related U.S. Application Data

(63) Continuation of application No. 13/955,393, filed on Jul. 31, 2013, now Pat. No. 10,071,243.

(51) Int. Cl.
| | | |
|---|---|---|
| *A61N 1/05* | (2006.01) | |
| *A61N 1/375* | (2006.01) | |
| *A61N 1/372* | (2006.01) | |

(52) U.S. Cl.
CPC ....... *A61N 1/0573* (2013.01); *A61N 1/37518* (2017.08); *A61N 1/059* (2013.01); *A61N 1/3756* (2013.01); *A61N 1/37205* (2013.01)

(58) Field of Classification Search
CPC ... A61N 1/0573; A61N 1/0556; A61N 1/0587
See application file for complete search history.

(56) References Cited

U.S. PATENT DOCUMENTS

| 721,869 A | 3/1903 | Dunning |
|---|---|---|
| 3,717,151 A | 2/1973 | Collett |
| (Continued) | | |

FOREIGN PATENT DOCUMENTS

| CA | 1003904 A1 | 1/1977 |
|---|---|---|
| CN | 1882370 | 12/2006 |
| (Continued) | | |

OTHER PUBLICATIONS

Chinese Office Action dated Sep. 6, 2016, Application No. 201480038011.7, English transaltion, 4 pages.

(Continued)

*Primary Examiner* — Paula J Stice
(74) *Attorney, Agent, or Firm* — Shumaker & Sieffert, P.A.

(57) ABSTRACT

A tine portion of an implantable medical device includes a hook segment and a distal segment terminated by a tissue-piercing tip, wherein the distal segment extends from a distal end of the hook segment to the tip. The hook segment, which is elastically deformable from a pre-set curvature, for example, defined by a single radius, preferably tapers from a first width thereof, in proximity to a proximal end thereof, to a smaller, second width thereof, in proximity to the distal end thereof, wherein the tip has a width that is greater than the second width of the hook segment. Alternately, the tine portion may include a hook segment that is defined by two radii and a straight section extending therebetween.

20 Claims, 19 Drawing Sheets

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,738,672 B2 | 5/2004 | Schulman et al. |
| 6,743,240 B2 | 6/2004 | Smith et al. |
| 6,755,812 B2 | 6/2004 | Peterson et al. |
| 6,823,217 B2 | 11/2004 | Rutten et al. |
| 6,909,920 B2 | 6/2005 | Lokhoff et al. |
| 6,944,507 B2 | 9/2005 | Froberg |
| 6,953,454 B2 | 10/2005 | Peterson et al. |
| 7,027,876 B2 | 4/2006 | Casavant et al. |
| 7,082,335 B2 | 7/2006 | Klein et al. |
| 7,082,336 B2 | 7/2006 | Ransbury et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,130,700 B2 | 10/2006 | Gardeski et al. |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,331,922 B2 | 2/2008 | Mohl |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,949,395 B2 | 5/2011 | Kuzma |
| 7,993,351 B2 | 8/2011 | Worley et al. |
| 8,010,209 B2 | 8/2011 | Jacobson |
| 8,012,127 B2 | 9/2011 | Lieberman et al. |
| 8,032,219 B2 | 10/2011 | Neumann et al. |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |

(56) References Cited

U.S. PATENT DOCUMENTS

| | | |
|---|---|---|
| 8,142,347 B2 | 3/2012 | Griego et al. |
| 8,160,722 B2 | 4/2012 | Rutten et al. |
| 8,170,690 B2 | 5/2012 | Morgan et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,262,672 B2 | 9/2012 | Neidert et al. |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,418,362 B2* | 4/2013 | Zerfas ............... A61B 18/1477 29/874 |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,700,181 B2 | 4/2014 | Bornzin et al. |
| 8,721,587 B2 | 5/2014 | Berthiaume et al. |
| 8,727,996 B2 | 5/2014 | Allan et al. |
| 8,738,147 B2 | 5/2014 | Hastings et al. |
| 8,755,909 B2 | 6/2014 | Sommer et al. |
| 8,758,365 B2 | 6/2014 | Bonner et al. |
| 9,119,959 B2 | 9/2015 | Rys et al. |
| 9,155,882 B2 | 10/2015 | Grubac et al. |
| 9,283,381 B2 | 3/2016 | Grubac |
| 9,414,857 B2 | 8/2016 | Wood et al. |
| 9,446,248 B2 | 9/2016 | Sheldon et al. |
| 9,526,891 B2 | 12/2016 | Eggen et al. |
| 9,539,423 B2 | 1/2017 | Bonner et al. |
| 10,071,243 B2 | 9/2018 | Kuhn et al. |
| 10,099,050 B2 | 10/2018 | Chen et al. |
| 2002/0077556 A1 | 6/2002 | Schwartz |
| 2002/0095203 A1 | 7/2002 | Thompson et al. |
| 2003/0004537 A1 | 1/2003 | Boyle et al. |
| 2003/0233139 A1 | 12/2003 | Chitre et al. |
| 2004/0034401 A1 | 2/2004 | Dahlberg |
| 2004/0147973 A1 | 7/2004 | Hauser |
| 2004/0176797 A1 | 9/2004 | Opolski |
| 2004/0230280 A1 | 11/2004 | Cates |
| 2004/0249417 A1 | 12/2004 | Ransbury et al. |
| 2005/0090890 A1 | 4/2005 | Wu et al. |
| 2005/0267555 A1 | 12/2005 | Marnfeldt et al. |
| 2006/0085039 A1 | 4/2006 | Hastings et al. |
| 2006/0247753 A1 | 11/2006 | Wenger et al. |
| 2007/0043414 A1 | 2/2007 | Fifer et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051863 A1 | 2/2008 | Schneider |
| 2009/0082827 A1 | 3/2009 | Kveen et al. |
| 2009/0082828 A1 | 3/2009 | Ostroff |
| 2009/0204170 A1 | 8/2009 | Hastings et al. |
| 2009/0281605 A1 | 11/2009 | Marnfeldt et al. |
| 2010/0131036 A1 | 5/2010 | Geistert et al. |
| 2010/0198288 A1 | 8/2010 | Ostroff |
| 2010/0211149 A1 | 8/2010 | Morgan et al. |
| 2011/0034939 A1 | 2/2011 | Kveen et al. |
| 2011/0054555 A1 | 3/2011 | Williams et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0251660 A1* | 10/2011 | Griswold ............ A61N 1/37205 607/126 |
| 2011/0251661 A1 | 10/2011 | Fifer et al. |
| 2011/0251662 A1 | 10/2011 | Griswold et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0108986 A1 | 5/2012 | Beasley |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0110127 A1 | 5/2013 | Bornzin et al. |
| 2013/0110219 A1 | 5/2013 | Bornzin et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0233345 A1 | 9/2013 | Baarsch et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0107723 A1 | 4/2014 | Hou et al. |
| 2014/0148815 A1 | 5/2014 | Wenzel et al. |
| 2014/0180306 A1 | 6/2014 | Grubac et al. |
| 2015/0039069 A1 | 2/2015 | Rys et al. |
| 2015/0039070 A1 | 2/2015 | Kuhn et al. |
| 2015/0039071 A1 | 2/2015 | Grubac et al. |
| 2015/0051616 A1 | 2/2015 | Hassl et al. |
| 2015/0051682 A1 | 2/2015 | Schmidt et al. |
| 2015/0094668 A1 | 4/2015 | Wood et al. |
| 2015/0352353 A1 | 12/2015 | Rys et al. |
| 2016/0001068 A1 | 1/2016 | Grubac et al. |
| 2016/0059002 A1 | 3/2016 | Grubac et al. |

(56) References Cited

U.S. PATENT DOCUMENTS

| | | | |
|---|---|---|---|
| 2016/0094668 A1 | 3/2016 | Chang et al. | |
| 2017/0209688 A1 | 7/2017 | Drake et al. | |

FOREIGN PATENT DOCUMENTS

| | | |
|---|---|---|
| CN | 1882370 A | 12/2006 |
| DE | 2053919 A1 | 5/1972 |
| EP | 0212955 A2 | 3/1987 |
| EP | 779080 B1 | 5/2003 |
| JP | H02-88666 | 7/1990 |
| JP | 05245215 A | 9/1993 |
| RU | 2011151104 | 6/2013 |
| WO | WO9520993 A2 | 8/1995 |
| WO | WO0102053 A1 | 1/2001 |
| WO | 03032807 A2 | 4/2003 |
| WO | 2004028348 A2 | 4/2004 |
| WO | 2009039400 A1 | 3/2009 |
| WO | 2009042295 A1 | 4/2009 |
| WO | 2010131157 A1 | 11/2010 |
| WO | 2012092067 A1 | 7/2012 |
| WO | 2012092074 A1 | 7/2012 |
| WO | WO12135530 A1 | 10/2012 |
| WO | 2014006471 A1 | 1/2014 |

OTHER PUBLICATIONS (PCT/US2014/047962)PCT Notification of Transmittal of the International Search Report and the Written Opinion of the International Searching Authority, dated Oct. 10, 2014, 11 pages.

International Search Report from Written Opinion from International Application No. PCT/US2014/047962, dated Feb. 5, 2015, 6 pp.

International Preliminary Report on Patentability from International Application No. PCT/US2014/047962, dated Feb. 2, 2016, 11 pp.

Chinese Office Action dated Sep. 6, 2016, Application No. 201480038011.7 Chinese translation, 9 pages.

Chinese Office Action dated Sep. 6, 2016, Application No. 201480038011.7 English translation, 4 pages.

U.S. Appl. No. 16/158,724, filed by Xin Chen et al., filed Oct. 12, 2018.

Prosecution History from U.S. Appl. No. 13/955,393, dated from Nov. 26, 2014 through Aug. 10, 2018, 104 pp.

Notice of Allowance from U.S. Appl. No. 15/410,161, dated Jun. 13, 2018, 5 pp.

"Homer Mammalok Gold," accessed on or about Jan. 19, 2017, accessed from http://www.mana-tech.com/factsheets/HomerMammalok.pdf, 1 pp.

Medtronic model Selectrsuretm™ 3830 manual, 2013, accessed on or about Jan. 19, 2017, 20 pp.

Merriam-Webster Definition of "Compound Curve," accessed on Apr. 25, 2017, https://merriam-webster.com/dictionary/compound%20curve, 4 pp.

Spickler, et al., "Totally Self-Contained Intracardiac Pacemaker," J. Electrocardiology, vol. 3, Nos. 3 & 4, pp. 325-331, 1970. (Applicant points out, in accordance with MPEP 609.04(a), that the year of publication, 1970 is sufficiently earlier than the effective U.S. filing date, so that the particular month of publication is not in issue.).

Prosecution History from U.S. Appl. No. 15/410,085, dated from Nov. 2, 2018 through Feb. 7, 2019, 17 pp.

Notice of Allowance from U.S. Appl. No. 15/410,085, dated Jun. 26, 2019, 8 pp.

Prosecution History from U.S. Appl. No. 16/158,724, dated from Oct. 12, 2018 to Nov. 29, 2018, 38 pp.

Response to Office Action dated Feb. 7, 2019, from U.S. Appl. No. 15/410,085, filed May 6, 2019, 13 pp.

\* cited by examiner

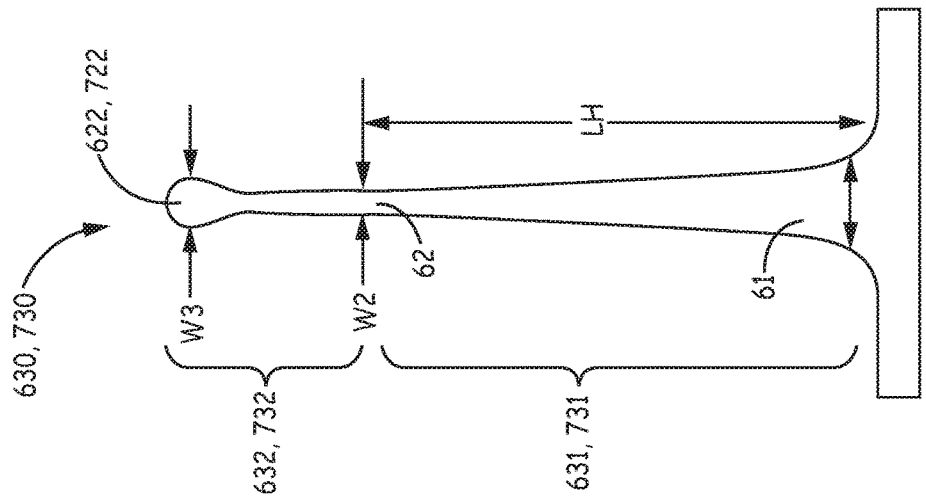
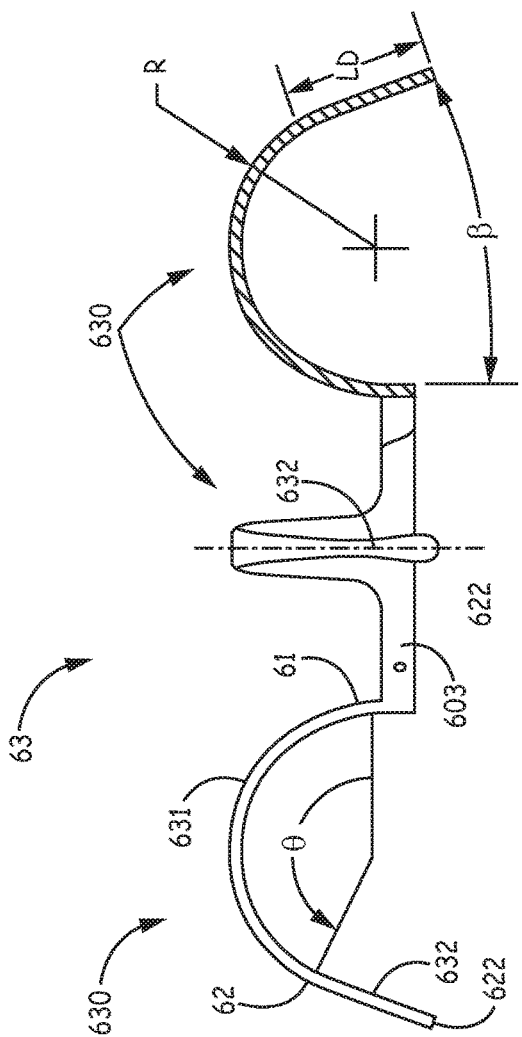
FIG. 6C
FIG. 6D

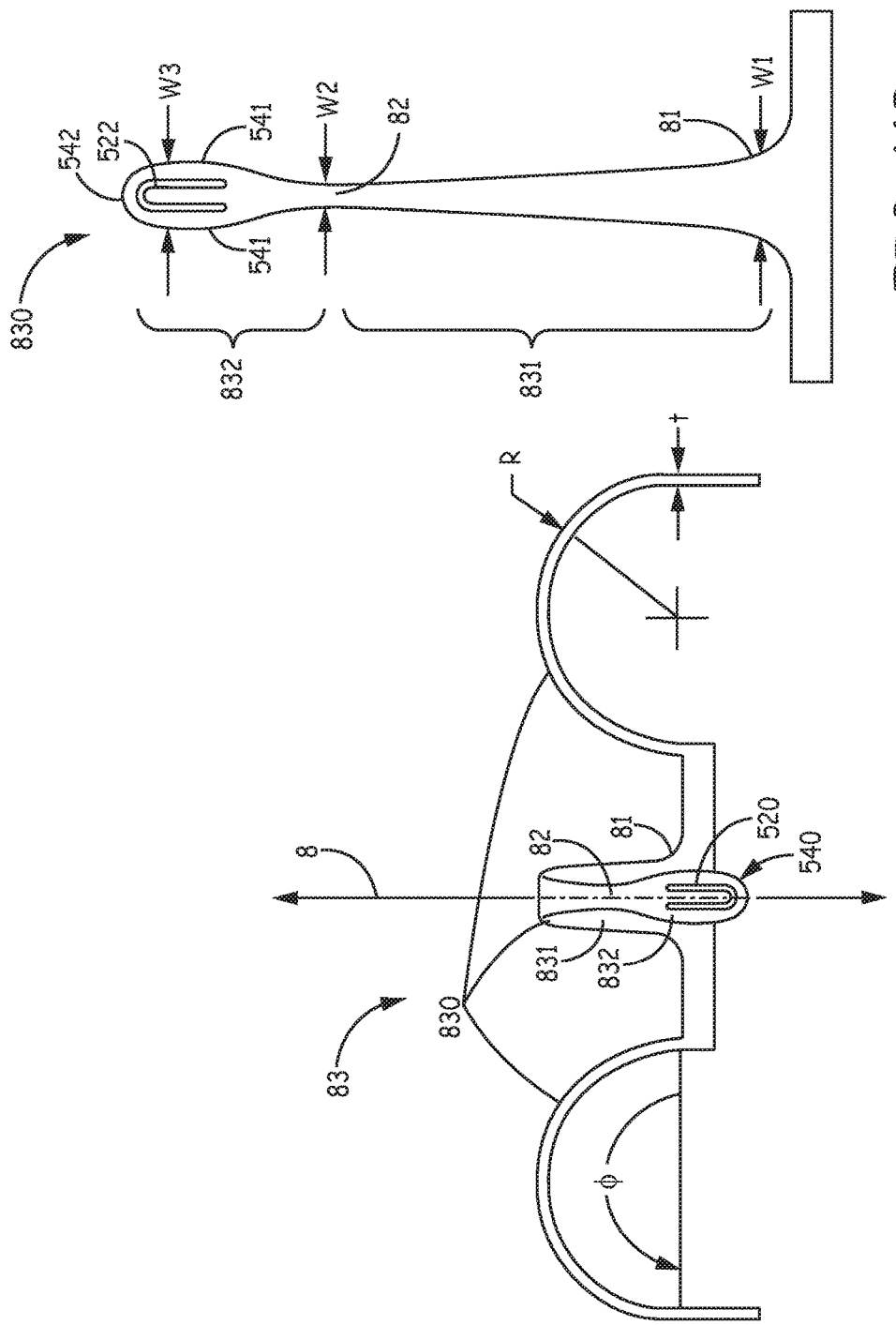

FIXATION FOR IMPLANTABLE MEDICAL DEVICES

CROSS-REFERENCE TO RELATED APPLICATION

This application is a Continuation of U.S. patent application Ser. No. 13/955,393, filed Jul. 31, 2013, the content of which is incorporated herein by reference in its entirety.

TECHNICAL FIELD

The present invention pertains to implantable medical devices, and, more specifically, to tissue-penetrating fixation components thereof.

BACKGROUND

An implantable medical device, for the delivery of stimulation therapy and/or for diagnostic sensing, may include at least one tissue-penetrating fixation component configured to hold the device at an implant location. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. FIG. 2 is a plan view of an exemplary implantable medical device 200, which includes a tissue-penetrating fixation component formed by a plurality of tine portions 230. FIG. 2 further illustrates device 200 including a hermitically sealed housing 220 that contains control electronics and a power source (not shown), and which defines a longitudinal axis 2 of device 200. Housing 220 may be formed from a medical grade stainless steel or titanium alloy and have an insulative layer formed thereover, for example, parylene, polyimide, or urethane. With further reference to FIG. 2, device 200 includes a pair of electrodes 261, 262, which may form a bipolar pair for cardiac pacing and sensing; tine portions 230 surround electrode 261 and are configured to penetrate tissue in order to hold electrode 261 in intimate contact with tissue, for example, at one of the aforementioned implant sites, while securing, or fixating device 200 for chronic implantation at the site. Further description of a suitable construction for device 200 may be found in the co-pending and commonly assigned United States patent application having the pre-grant publication number 2012/0172690 A1.

With reference to FIG. 3A, device 200 may be delivered to an implant location via a delivery catheter 300. For example, with reference to FIG. 1, if the target implant site is located in the right atrium RA, coronary vein CV, or right ventricle RV, a distal end 310 of catheter 300 may be maneuvered into the heart through a superior vena cava SVC or an inferior vena cava IVC, according to a transvenous delivery method known in the art. FIG. 3A shows a partial cross-section of distal end 310 of catheter 300, which is formed like a cup to hold and contain device 200 for delivery to the implant site. FIG. 3A illustrates device 200 having been loaded into distal end 310 so that a hook segment 231 of each tine portion 230 is elastically deformed, from a pre-set curvature thereof, to an open position, at which a distal segment 232 of each tine portion 230 extends distally toward an opening 313 of catheter distal end 310. Each tine portion 230 is preferably formed from a superelastic material, such as Nitinol. FIG. 3A further illustrates a deployment element 320 abutting a proximal end of device 200 and extending proximally therefrom, through a lumen of catheter 300, and out from a proximal opening 301 thereof. Element 320 may be moved, per arrow M, by an operator to push device 200, per arrow P, out from opening 313 of distal end 310, for example, when opening 313 has been located by the operator in close proximity to tissue at the target implant site.

FIG. 3B, is an enlarged view of distal segment 232 of one of tine portions 230, wherein a tissue-piercing tip 322, which terminates distal segment 232, has just been pushed out through opening 313 of distal end 310 of catheter 300 and into contact with tissue T. FIG. 3B illustrates distal segment 232 supported by the surrounding wall of distal end 310, in proximity to opening 313, so that the push force of deployment element 320 is effectively transferred through tip 322 to first compress the tissue T, as shown, and then to pierce the tissue T for penetration therein, which is shown in FIGS. 3C-D. FIGS. 3C-D illustrate partial tine penetration and full tine penetration, respectively, as deployment element 320 continues to push device 200 out opening 313. It can be seen that the elastic nature of each tine portion 230, once the constraint of the distal end 310 is withdrawn, allows the corresponding hook segment 231 to relax back toward the pre-set curvature thereof within the tissue. The full penetration of tine portions 230, shown FIG. 3D, is representative of acute fixation of device 200 at the implant site, for example, for the evaluation of device performance (e.g., pacing and sensing via electrodes 261, 262). It should be noted that, at some implant sites, tine portions 230 may, at full penetration, extend back out from tissue T, for example, generally toward distal end 310 of catheter 300.

With further reference to FIG. 3D, a tether 350 is shown looping through an eye feature 205 formed at the proximal end of device 200; tether 350 extends proximally through a lumen of deployment element 320 to a proximal end 351 thereof, outside a proximal end of deployment element 320, which may be seen in FIG. 3A. Thus, if the performance of acutely fixated device 200 is unsatisfactory, the operator may use tether 350 to pull device 200 back into distal end 310, thereby withdrawing tine portions 230 from the tissue, so that device may be moved by delivery catheter 300 to another potential implant site. Alternately, if the acutely fixated device 200 performs satisfactorily, proximal end 351 of tether 350 may be severed to pull tether 350 out from eye feature 205 of device 200, and the fully penetrated tine portions 230 continue to fixate device 200 for chronic implant.

The aforementioned co-pending and commonly assigned U.S. patent application '690 discloses suitable embodiments of a fixation component having tine portions similar to tine portions 230, wherein the tine portions exhibit a suitable baseline performance, for example, in terms of a deployment force, an acute retraction force (for repositioning), atraumatic retraction, and acute and chronic fixation forces. Yet, there is still a need for new configurations of tine portions for implantable devices, like device 200, that may further enhance fixation.

SUMMARY

Some embodiments of the present invention encompass implantable medical devices (e.g., cardiac pacemakers) and tissue-penetrating fixation components thereof, which include one or more tine portions configured for increased strain relief during the flexing thereof, either at initial implant (particularly in cases where the retraction of penetrated tines is necessary for repositioning the device), or when subject to cyclic loading during a chronic implant of the fixated device, for example, within a beating heart. These tine portions are, preferably, also configured to reduce the risk of tissue trauma during the retraction thereof from the tissue, for example, for repositioning. In certain embodiments, a tissue-penetrating fixation component for an implantable medical device includes a tine portion configured to mitigate the risk of compressing, for example, to the point of occlusion, blood vessels in proximity to the implant site, without sacrificing chronic fixation performance, and while maintaining adequate strain relief.

According to some embodiments, a tine portion of a tissue-penetrating component of an implantable medical device includes a hook segment and a distal segment terminated by a tissue-piercing tip. The hook segment, which is pre-set to extend along a curvature that encloses an angle of between 135 degrees and 270 degrees, from a proximal end thereof, in proximity to the base portion, to a distal end thereof, and which is elastically deformable from the pre-set curvature to an open position, tapers from a first width thereof, in proximity to the proximal end thereof, to a second width thereof, in proximity to the distal end thereof, the second width being less than the first width. The distal segment, which is pre-set to extend along a relatively straight line, approximately tangent to the distal end of the hook segment, from the distal end of the hook segment, is terminated by a tissue-piercing tip that, preferably, has a width that is greater than the second width of the hook segment. The first width of the hook segment may be approximately two to five times greater than the second width thereof, and the width of the tissue-piercing tip may be two to three times greater than the second width.

According to some embodiments, in which a length of the distal segment of the tine portion is relatively short, to mitigate the risk of vessel compression, the distal segment either extends approximately parallel to a longitudinal axis of the component/device, or away from the longitudinal axis, when the hook segment conforms to the pre-set curvature.

According to some embodiments, in which the tissue-penetrating component further includes a base portion, for example, in the form of a ring, that defines the aforementioned longitudinal axis and is configured to be fixedly attached to the implantable medical device, the tine portion further includes a proximal segment that extends between the hook segment and the base portion, wherein the proximal segment may extend from the base portion toward the longitudinal axis.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 6C is an elevation view of the component of FIG. 7B, according to some embodiments;

FIG. 6D is a plan view of a tine portion of the component of FIG. 7B, according to some embodiments;

FIG. 11A is an elevation view of a tissue-penetrating fixation component, according to yet further embodiments of the present invention, which may be incorporated in the exemplary device of FIG. 10A; and FIG. 11B is a plan view of a tine portion of the component of FIG. 11A, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 3A:
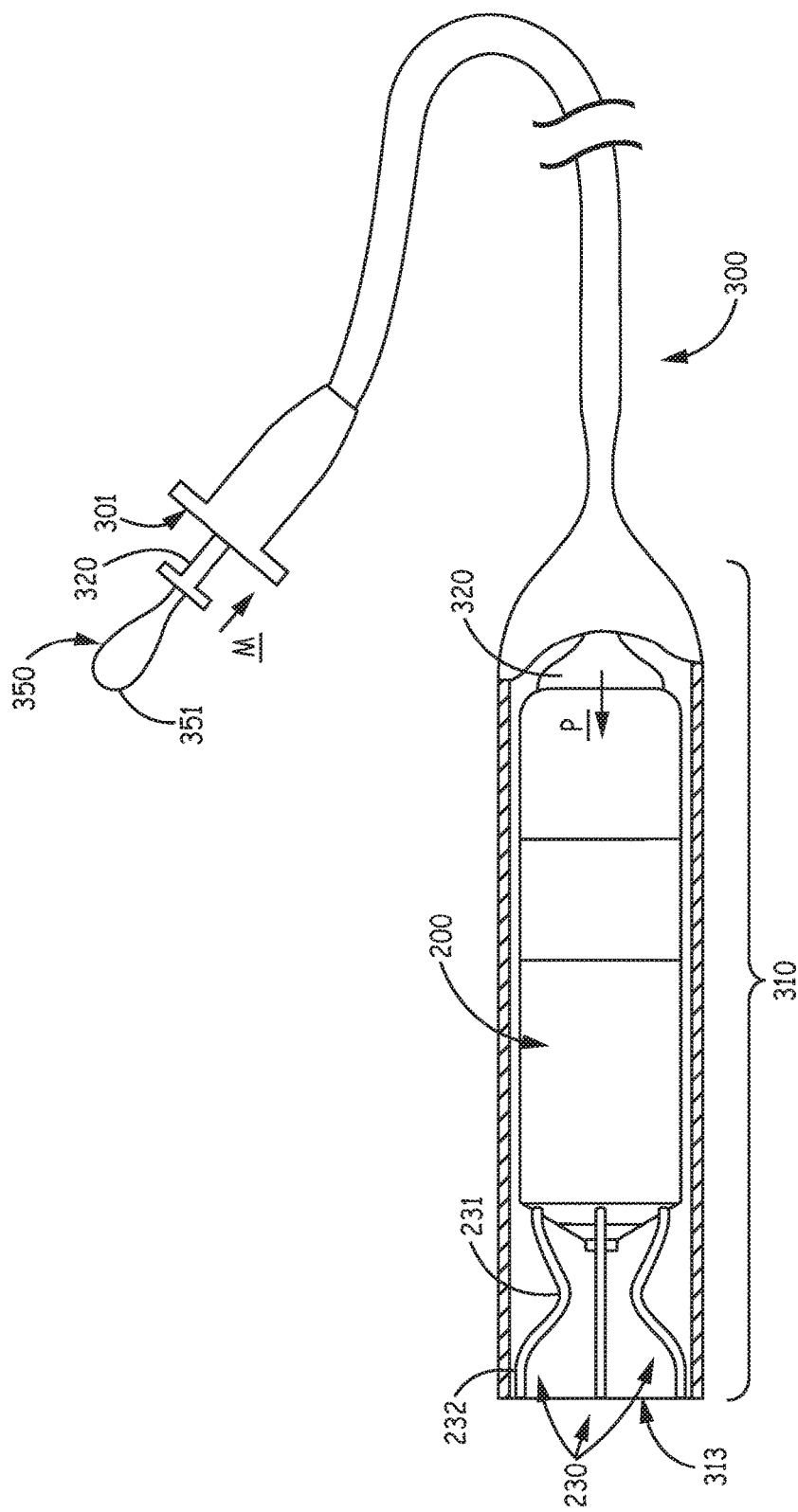
FIG. 3A is a plan view of the medical device loaded in a delivery catheter, according to some embodiments, wherein tine portions of a tissue-penetrating fixation component thereof are elastically deformed into an open position.
Figure 3B:
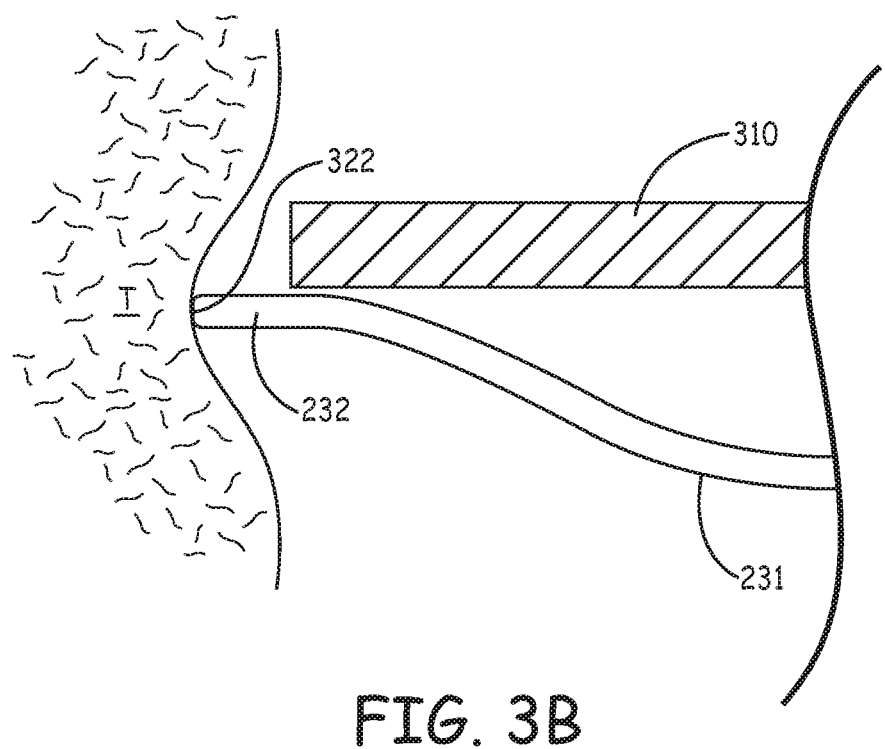
FIG. 3B is an enlarged detail view of one of the tine portions initially contacting tissue at an implant site.
Figure 3C:
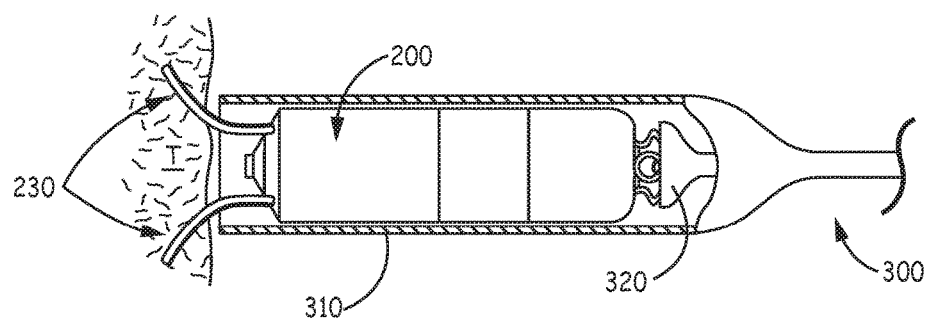
FIGS. 3C-D are plan views of the device and catheter in subsequent steps of implanting the device, when the tine portions have penetrated the tissue.
Figure 3D:
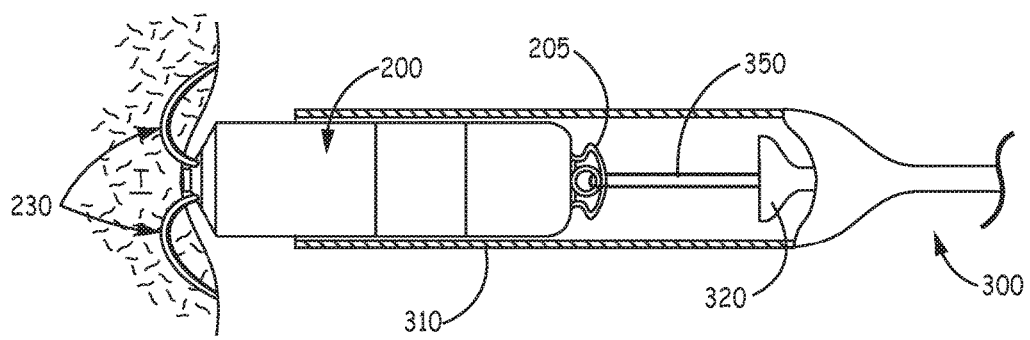
Figure 4B:
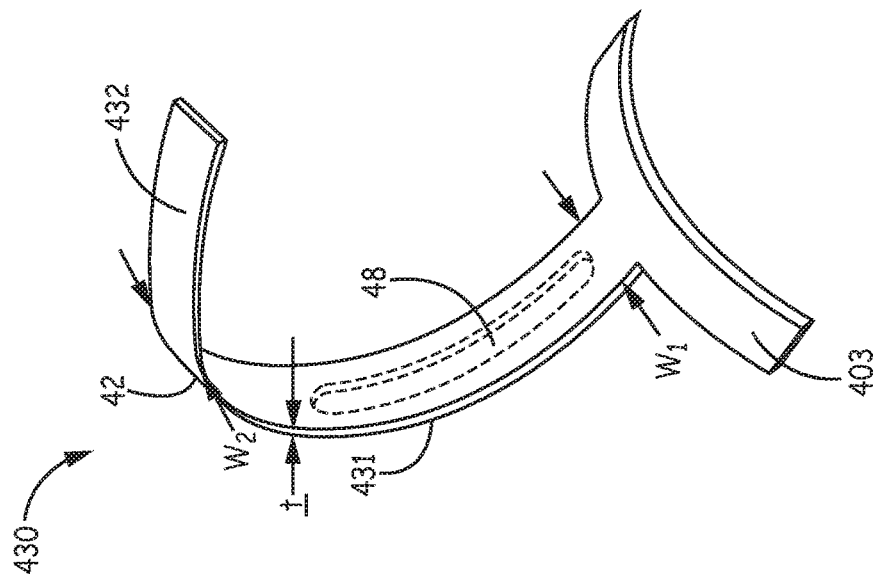
FIG. 4B is a perspective view of a tapered tine portion, according to some embodiments of the present invention.
Figure 4A:
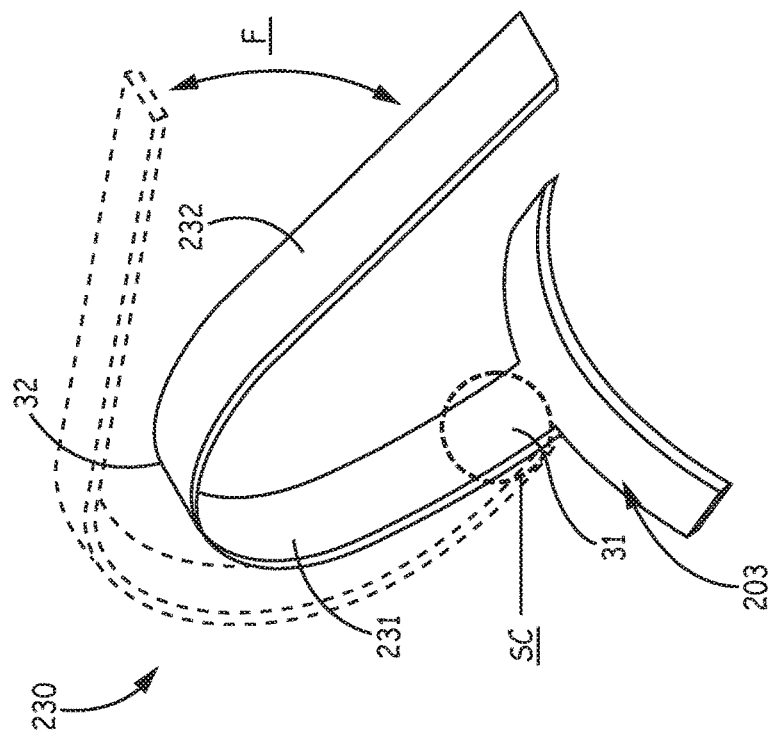
FIG. 4A is a schematic representation of a flexing tine portion.

FIG. 4A is a schematic representation of one of tine portions 230 isolated from the above-described implantable medical device 200, wherein an exemplary flexing, per arrow F, of tine portion 230 is illustrated. Such flexing may be encountered by tine portion 230, once tine portion 230 has penetrated tissue to fix device 200 at a chronic implant site for cardiac monitoring and/or therapy, for example, as illustrated in FIG. 3D. Thus, fatigue life is a consideration influencing the configuration of tine portions for those implantable medical devices that may be subjected to cyclic loading caused by hundreds of millions of heart beats, over the life of their implant. In FIG. 4A, a zone of stress concentration SC, for example, in response to the flexing per arrow F, is circled; zone SC is located in proximity to a proximal end 31 of hook segment 231 of tine portion 230, where hook segment 231 joins with a base portion 203. Base portion 203 and tine portion 230 may be integrally formed, wherein base portion 203 is configured to be fixedly attached to device 200. Stress concentration in zone SC may also result from deformation of hook segment 231 into the open position (FIG. 3A), for example, upon initial loading of device 200 and retraction of device 200 back into distal end 310 of catheter for repositioning, which, in combination with the repeated force of deployment, can potentially push tine portion 230 toward an elastic limit and may make tine portion 230 subsequently more vulnerable to fatigue under the aforementioned cyclic loading. Although rounded edges of tine portions 230 effectively reduce the concentration of stress, as previously described in the aforementioned commonly-assigned U.S. patent application '690, some embodiments of the present invention incorporate tine portions that have tapered hook segments to further address the stress concentration, for example, as illustrated in FIG. 4B.

FIG. 4B is a perspective view of a tine portion 430, according to some embodiments, one or more of which may be integrated into device 200, as substitute for tine portions 230. A base portion 403 is shown integrally formed with tine portion 430, according to some preferred embodiments, wherein base portion 403 is configured for attachment to a medical device, such as device 200. FIG. 4B illustrates a hook segment 431 of tine portion 430 extending from a first end 41 thereof, in proximity to base portion 403, to a second end 42 thereof, in proximity to a distal segment 432 of tine portion 430, wherein hook segment 431 tapers from a first width W1, in proximity to proximal end 41, to a smaller, second width W2, in proximity to a distal end 42 of hook segment 431. The tapering of hook segment 431 provides strain relief during the aforementioned deformation/flexing, to alleviate the aforementioned stress concentration. FIG. 4B further illustrates an optional slot 48 (dashed lines), which may be formed through a thickness t of tine portion 430, and extend between first width W1 and second width W2. The inclusion of slot 48 provides an additional means for providing strain relief, for example, when a limit on how narrow second width W2 may be, for example, no smaller than approximately 0.020-0.025 inch, so that distal segment 432 does not tear tissue upon retraction therefrom. According to some embodiments, optional slot 48 may include internal shear tabs (not shown) to help distribute out of plane loads, for example, orthogonal to the illustrated direction of flexing, per arrow F of FIG. 4A.

With further reference to FIGS. 4A-B, distal segment 432 of tine portion 430 is shown having a shorter length than distal segment 232 of tine portion 230, for example, to provide more flexibility in selecting a suitable implant site without risking undue trauma to tissue, upon penetration of tine portion 430 at the selected site. The shorter length can help to prevent perforation through the wall of a structure, for example, the heart, at some implant locations, and can reduce a probability for penetrated tine portions 430 to interfere with blood vessels, which interference, for example, may compromise coronary blood supply, as will be described below in conjunction with FIG. 5.

Figure 2:
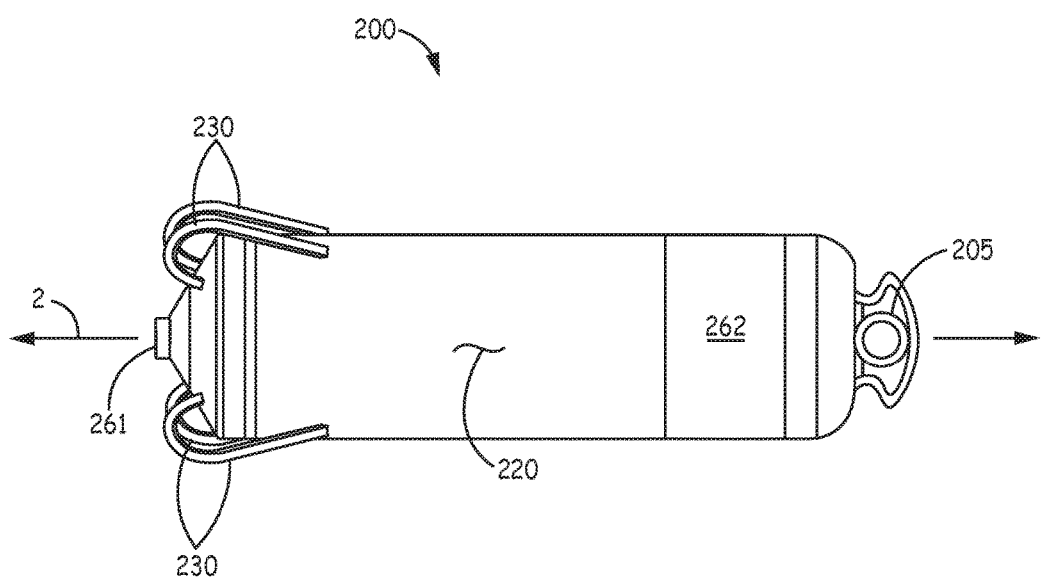
FIG. 2 is a plan view of an exemplary implantable medical device.
Figure 5:
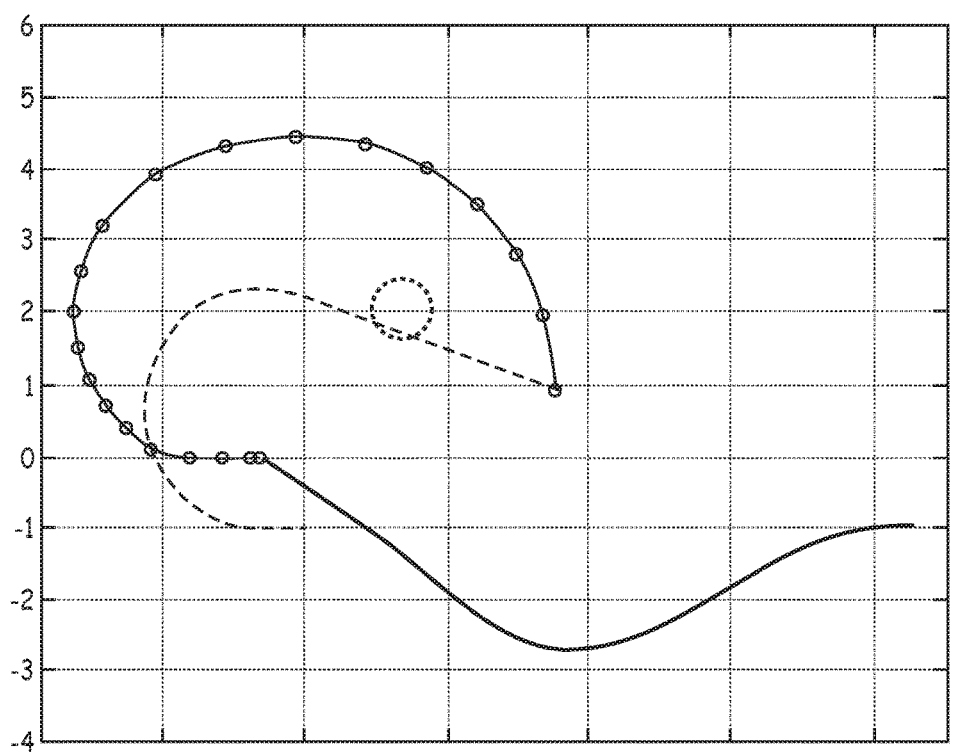
FIG. 5 is an estimated penetration path and an 'as set' relaxation plot for a tine portion of the exemplary device shown in FIG. 2.

FIG. 5 is an estimated tissue penetration path and an 'as set' relaxation plot for tine portion 230 of device 200 (FIG. 2), wherein tine portion 230 is formed from approximately 0.005 inch thick Nitinol. FIG. 5 includes a solid line, which represents the profile of tine portion 230 when device 200 is loaded in distal end 310 of catheter 300 (FIG. 3A) with hook segment 231 deformed to the open position. With reference back to FIGS. 3A-D, the origin, or zero coordinate, along the ordinate axis generally corresponds to the constraining wall of distal segment 310 of delivery catheter 300. The plot of FIG. 5 is made up of a segmented line connecting circles, which corresponds to the estimated penetration path of tine portion 230, for example, when device 200 is pushed out from distal end 310 and into tissue T (FIGS. 3B-D), and a dashed line, which represents the profile of tine portion 230, according to the pre-set curvature, toward which the penetrated tine portion 230 relaxes over time. The volume of tissue between the segmented line and the dashed line approaches that which is squeezed or compressed by the penetrated tine portion 230 as it relaxes over time; the greater this volume, the greater the probability for the penetrated tine to compress or pinch one or more blood vessels that perfuse the tissue. For example, the dotted line in FIG. 5 represents a potential coronary artery that may be compressed or pinched by tine portion 230. As alluded to above, the length of distal segment 232 is a factor contributing to the volume that is squeezed by penetrated tine portion 230, so that reducing the length of distal segment 232 may be desired. However, if the length of distal segment 232 is reduced, without modifying other aspects of tine portion 230, an orientation of tine portion 230 relative to tissue T, when hook segment 231 is in the open position, will be impacted such that tine portion 230 may be less likely to effectively penetrate into tissue T, for example, upon exiting through opening 313 of distal end 310 of catheter 300 (FIGS. 3A-B). Therefore, with reference to FIG. 4B, the tapering of hook segment 431 of tine portion 430 not only relieves strain but also allows for a more favorable orientation of the shorter distal segment 432 for tissue penetration (e.g., being directed along a line that is closer to normal to the tissue surface), when hook segment 431 is in the open position.

Various embodiments of tine portions for fixation of an implantable medical device, for example, as described below, incorporate a tapered hook segment and/or a shorter distal segment, to address the above described cyclic loading and/or potential tissue trauma. The following embodiments have been configured with reference to prior art tine portions of tissue-penetrating fixation components for medical devices, such as those described in the aforementioned commonly assigned U.S. patent application '690 (generally corresponding to tine portion 230), in order to allow a similar fit of devices, like device 200, within a delivery catheter, for example, having the tine portions deformed into the open position within distal portion 310 of catheter 300, and to maintain suitable baseline performance, for example, in terms of a deployment force (e.g., no greater than approximately 1-2 Newtons for a fixation component having four tine portions), an acute retraction force, for repositioning (e.g., between approximately 3-4 Newtons for a fixation component having four tine portions), atraumatic retraction, and an adequate acute fixation force (e.g., greater than approximately 2.5 Newtons for a fixation component having four tine portions).

Figure 6A:
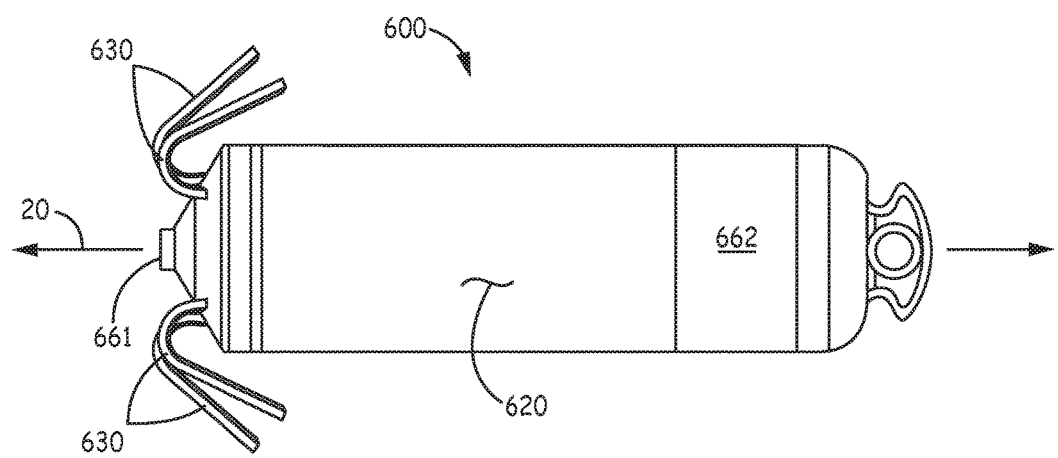
FIG. 6A is a plan view of an implantable medical device, according to some embodiments of the present invention.

FIG. 6A is a plan view of a medical device 600, according to some embodiments of the present invention. FIG. 6A illustrates device 600 including a hermetically sealed housing 620 and a pair of electrodes 661, 662; housing 620, like housing 220 of device 200, contains control electronics and a power source (not shown), which, for example, together with electrodes 661, 662, are adapted for cardiac pacing and sensing. FIG. 6A further illustrates device 600 including tine portions 630, which are adapted to penetrate tissue in order to secure device 600 at an implant site, for example, a cardiac site in the right atrium RA or the right ventricle RV (FIG. 1), having been deployed from distal end 310 of delivery catheter 300 (FIGS. 3A-D). According to some embodiments, tine portions 630 are included in a tissue-penetrating fixation component 63, which is shown, separate from device 600, in FIG. 6B.

Figure 6B:
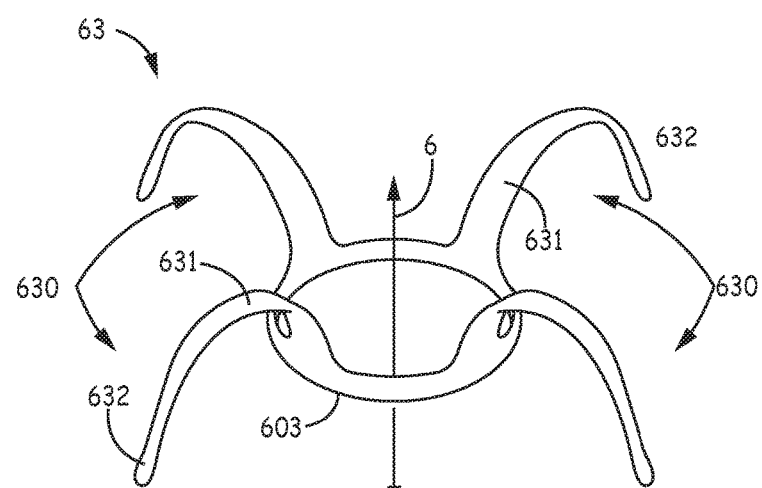
FIG. 6B is a perspective view of a tissue-penetrating fixation component, according to some embodiments of the present invention, separated from the device of FIG. 6A.

FIG. 6B illustrates component 63 also including a base portion 603, from which tine portions 630 extend, preferably being integrally formed therewith, as described below. According to the illustrated embodiment, base portion 603 of fixation component 63 defines a longitudinal axis 6 of component 63 and is configured for attachment to device 600 so that axis 6 is approximately aligned with a longitudinal axis 20 of device 600. Component 63 may be part of a subassembly that forms a distal end of device 600, and which also includes electrode 661; such a subassembly is described in the aforementioned commonly-assigned U.S. patent application '690, in conjunction with FIGS. 3A-4B thereof, the description of which is hereby incorporated by reference. FIG. 6B further illustrates each tine portion 630 of tissue-penetrating component 63 including a hook segment 631 and a distal segment 632.

With reference to FIG. 6C, which is an elevation view of component 63, each hook segment 631 extends along a pre-set curvature that encloses an angle θ, from a proximal end 61 thereof to a distal end 62 thereof. FIG. 6C illustrates each distal segment 632 extending along a relatively straight line that is approximately tangent to distal end 62 of hook segment 631. According to the illustrated embodiment, angle θ is less than 180 degrees, such that distal segment 632 extends away from axis 6. FIG. 6C further illustrates the preset curvature of hook segment 631 being defined by a single radius R. According to an exemplary embodiment, radius R is approximately 0.085 inch, an angle β, at which distal segment extends relative to axis 6, is approximately 20 degrees, and a length LD of distal segment 632 is between approximately 0.05 inch and approximately 0.1 inch.

According to some preferred embodiments, component 63 is manufactured by, first, laser cutting base portion 603 and tine portions 630, together, from a tube of superelastic and biocompatible metal (e.g., Nitinol), and then wrapping and holding each tine portion 630 about a mandrel for a heat setting process that pre-sets the illustrated curvature of each hook segment 631. Manufacturing methods such as these are known to those skilled in the art of forming Nitinol components. Although FIG. 6B shows base portion 603 of component 63 formed as a ring, wherein tine portions 630 are integrally formed therewith and spaced apart from one another about a perimeter of the ring, in alternate embodiments of tissue penetrating fixation components, one or more tine portions may be formed individually and then attached to a base portion that is configured in any suitable fashion for attachment to device 600.

FIG. 6D is a plan view of one of tine portions 630, prior to forming the pre-set curvature thereof, in which the above-described tapering for strain relief along hook segment 631, from first width W1 to smaller, second width W2 may be seen. When, for example, in the aforementioned exemplary embodiment, component 63 is manufactured from Nitinol tubing that has a thickness of approximately 0.005 inch, and hook segment 631 thereof has a length LH of approximately 0.23 inch, first width W1 may be between approximately two to five times greater than second width W2 to provide strain relief for improved fatigue life. Yet, if the smaller, second width W2, for example, being approximately 0.010 inch, were to define an entirety of distal segment 632, distal segment 632 may tear tissue upon retraction therefrom, for example, when repositioning device 600. So, with further reference to FIG. 6D, distal segment 632 of tine portion 630 is terminated by a tissue-piercing tip 622 that has a width W3, which is greater than second width W2, for example, approximately two to three times greater, in order to be atraumatic to tissue. In the aforementioned exemplary embodiment, first width W1 is between approximately 0.034 inch and approximately 0.05 inch, second width W2 is approximately 0.010 inch, and third width W3 is approximately 0.02 inch.

Figure 7A:
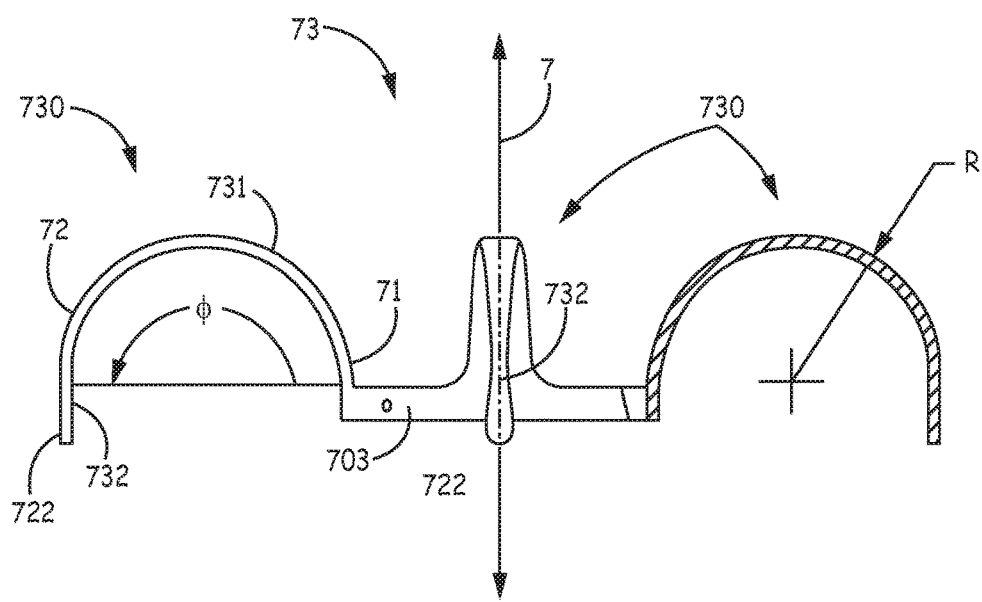
FIG. 7A is an elevation view of a tissue-penetrating fixation component, according to some alternate embodiments, which may be incorporated in the device of FIG. 6A.

FIG. 7A is an elevation view of a tissue-penetrating fixation component 73, according to some alternate embodiments of the present invention, which may be incorporated in device 600 as an alternative to component 63, such that a longitudinal axis 7 of component 73 is approximately aligned with longitudinal axis 20 of device 600. FIG. 7A illustrates component 73 including a base portion 703, similar to base portion 603 of component 63, and a plurality of tine portions 730, each of which includes a hook segment 731 and a distal segment 732. Tine portions 730 and base portion 703 are preferably integrally formed according to the method described above for component 63. Furthermore, each tine portion 730, prior to the pre-setting of a curvature of hook segment 731, may be configured like tine portion 630 as described above in conjunction with FIG. 6D, wherein the aforementioned exemplary values for widths W1, W2, W3, thickness t and lengths LD, LH are suitable. However, with further reference to FIG. 7A, the pre-set curvature along which hook segment 731 extends, from a first end 71 thereof and a second end 72 thereof, encloses an angle φ, which is 180 degrees, so that distal segment 732 extends, between a tissue-piercing tip 722 thereof and second end 72 of hook segment 731, along a line that is approximately parallel to axis 7. The pre-set curvature of hook segment 731, like hook segment 631, is defined by a single radius R, which may be approximately 0.085 inch.

Figure 7B:
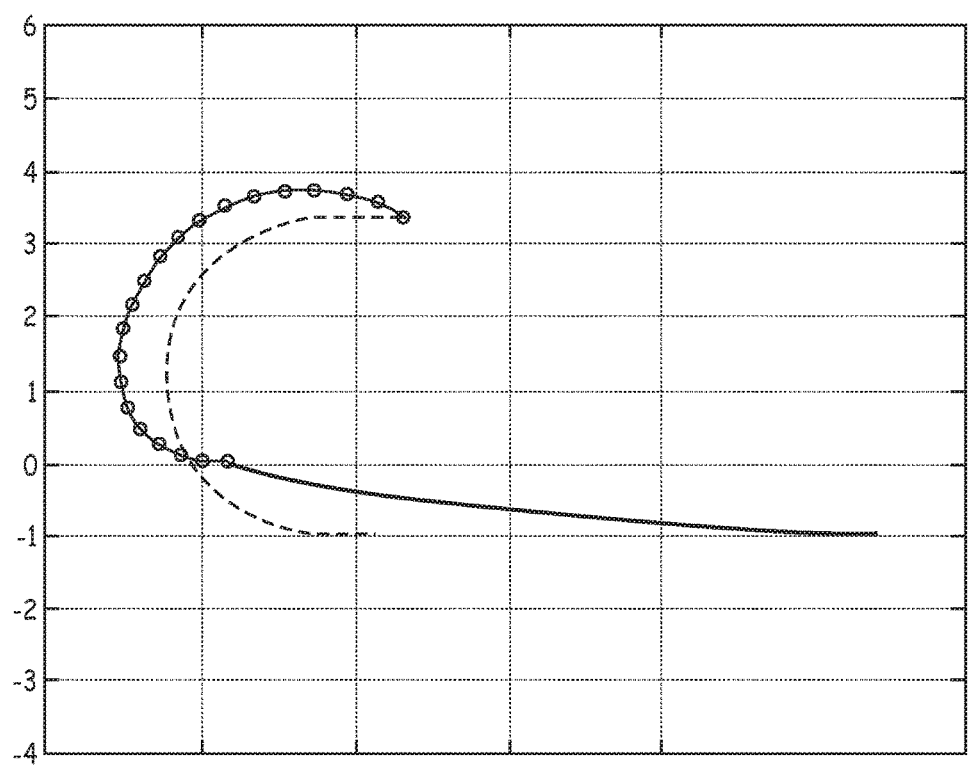
FIG. 7B is an estimated penetration path and an 'as set' relaxation plot for a tine portion of the component shown in FIG. 7A.

FIG. 7B is an estimated penetration path and an 'as set' relaxation plot for tine portion 730 of component 73, which may be compared to that of tine portion 230 (FIG. 5). FIG. 7B illustrates, with a solid line, tine portion 730 having been elastically deformed into the open position, for example, as would be the case when device 600 includes component 73 and is loaded within a delivery catheter, for example, distal end 310 of delivery catheter 300 (FIG. 3A). In comparing the solid lines of FIGS. 5 and 7B, it may be appreciated how the strain relief of tapering flattens the deformed profile of tine portion 730 relative to that of tine portion 230, and that the open position of tine portion 730 orients distal segment 732 of tine portion 730 along a line that is nearly normal to the ordinate axis, which generally corresponds to the above-described tissue surface, for effective tissue penetration. Furthermore, in comparing the estimated tissue penetration path of tine portions 230 and 730 (segmented lines connecting the circles), relative to the corresponding relaxed profiles (dashed lines), it can be seen that, due to the shorter length and more open pre-set curvature, tine portion 730 does not encompass as large a volume of tissue, relative to the pre-set curvature, toward which the penetrated tine portion 730 relaxes over time, upon full penetration, so that the above described risk of perforation and/or pinching of blood vessels is reduced.

Figure 8A:
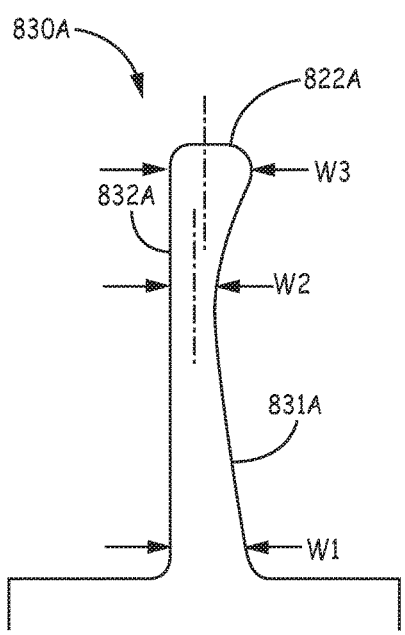
FIGS. 8A-B are plan views of tine portions, according to some alternate embodiments.
Figure 8B:
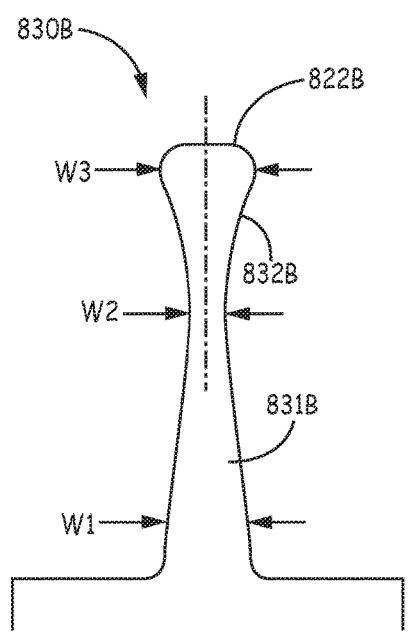

FIGS. 8A-B are plan views of tine portions 830A, 830B, prior to pre-setting a curvature thereof, according to some alternate embodiments, either of which may be formed in component 63, 73 in lieu of tine portions 630, 730, for example, to increase the ease of tolerance control and inspection. FIGS. 8A-B illustrate hook segments 831A, 831B of tine portions 830A, 830B having a single-sided, or asymmetric taper. According to the illustrated embodiments, widths W1, W2, and W3 are designated at generally the same locations along hook segments 831A, 831B and distal segments 832A, 832B, as previously described for tine portions 630 and 730. Furthermore, it should be understood that, according to some preferred embodiments, a thickness of each tine portion 830A, 830B (into the page), for example, approximately 0.005 inch, is approximately constant along an entire length of each tine portion 830A, 830B, since components that would include tine portions 830A, 830B are preferably formed from a Nitinol tube according to the method described above. FIG. 8A further illustrates distal segment 832A of tine portion 830A being terminated in a tissue-piercing tip 822, at which width W3 has a center line that is offset from a center line of second width W2; while FIG. 8B illustrates a tissue-piercing tip 822B of distal segment 832B, at which width W3 has a center line approximately aligned with that of second width W2. According to some exemplary embodiments, first width W1 is between approximately 0.034 inch and approximately 0.05 inch, second width W2 is approximately 0.010 inch, and third width W3 is approximately 0.02 inch.

FIGS. 9A-D are profiles and corresponding estimated penetration path and 'as set' relaxation plots of various tine portions 930A, 930B, 930C, 930D, according to yet further embodiments of the present invention, wherein the profiles, per the pre-set curvatures of hook segments 931A-D, accommodate for a relatively shorter length of distal segments 932A-D thereof, for example, compared to that of tine portion 230 (FIG. 5). FIGS. 9A-D illustrate the pre-set curvature of each hook segment 931A-D being defined by two radii, R1 and R2, wherein R2 is greater than R1. According to exemplary embodiments of tine portions 930A, 930B, radius R1 is approximately 1.04 mm and radius R2 is approximately 1.65 mm, while in an exemplary embodiment of tine portion 930C, radius R1 is approximately 0.5 mm and radius R2 is approximately 1.65 mm, and, in an exemplary embodiment of tine portion 930D, radius R1 is 0.25 mm and radius R2 is approximately 2.4 mm. It should be noted that none of tine portions 930A-D, as depicted in the corresponding plots, include tapering along the corresponding hook segments 931A-D thereof. Yet, it is contemplated that a tapering of hook segments 931A-D, for example, similar to that described above, will provide strain relief for improved fatigue life and allow for shorter tine portions 930A-D without compromising the orientation of distal segments 932A-D, when hook segments 931A-D are deformed into the open position.

Each of tine portions 930A-D may be one of a plurality, which are included in a tissue-penetrating component, and that extend from a base portion 903 of the component, wherein base portion 903 defines an axis 9 of the component, and may be similar to the above described base portions 603, 703 of components 63, 73. FIGS. 9A-D further illustrate each of tine portions 930A-D including a proximal segment 933A-D that extends between base portion 903 and the corresponding hook portion 931A-D. Each of proximal segments 933A, 933B is shown extending approximately parallel to axis 9, while each of proximal segments 933C, 933D is shown extending from base portion 903 toward axis 9, for example, to increase an overall arc length of each of tine portions 930C, 930D for added flexibility during retraction into catheter distal end 310 (FIGS. 3A-C), when the corresponding hook segment 931C, 931D is being elastically deformed to the open position (solid line of plots). Furthermore, although the orientation of distal segments 932C, 932D, when tine portions 930C, 930D are in the open position, is less favorable for ease of tissue penetration that of other embodiments, the extension of proximal segments 933C, 933D toward axis 9 can contribute to a reduction in compressed tissue volume without a tapering of hook segments 931C, 931D.

Figure 9A:
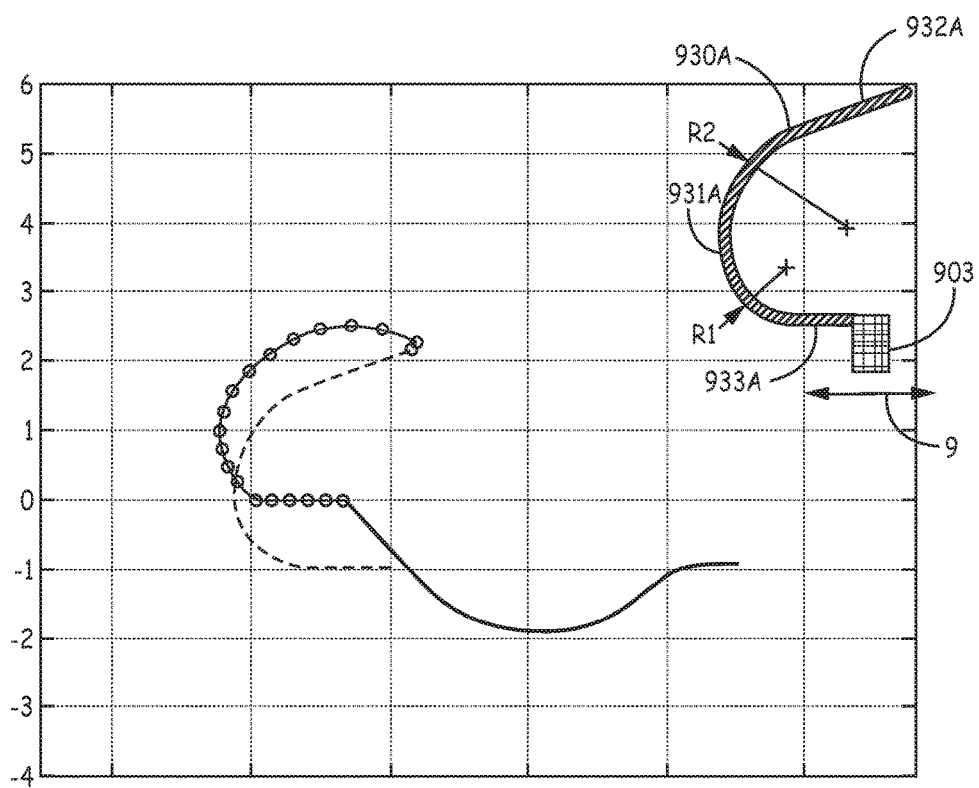
FIGS. 9A-D are profiles and corresponding estimated penetration path and 'as set' relaxation plots of various tine portions, according to additional embodiments.
Figure 9B:
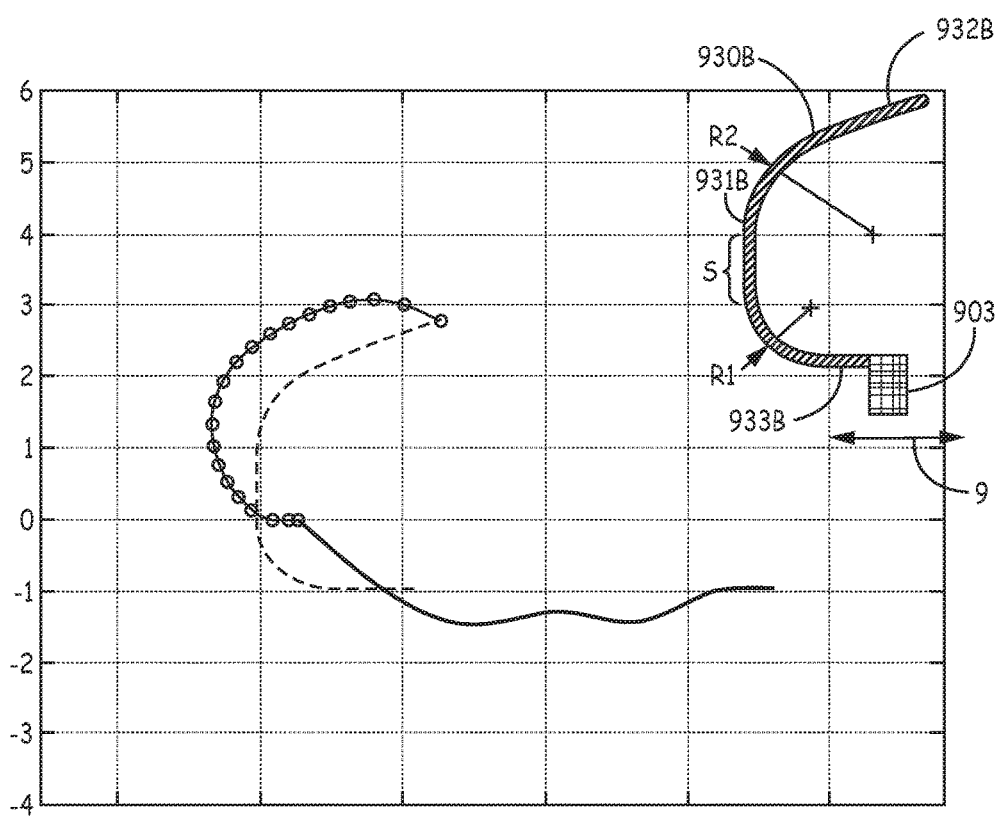
Figure 9C:
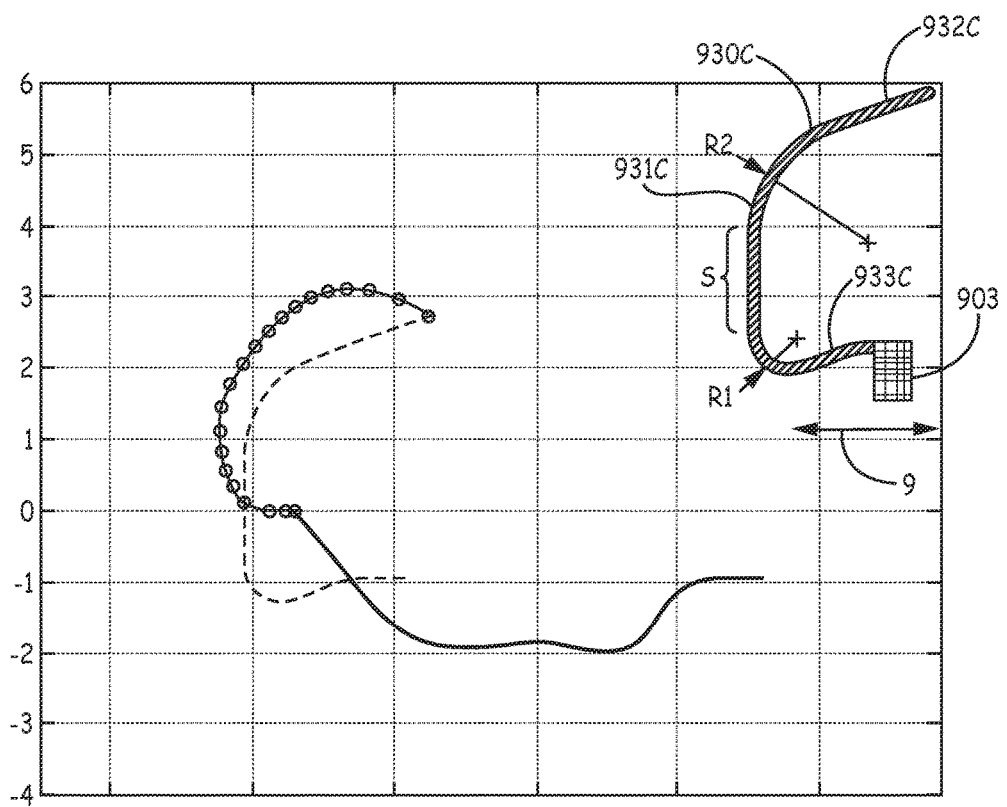
Figure 9D:
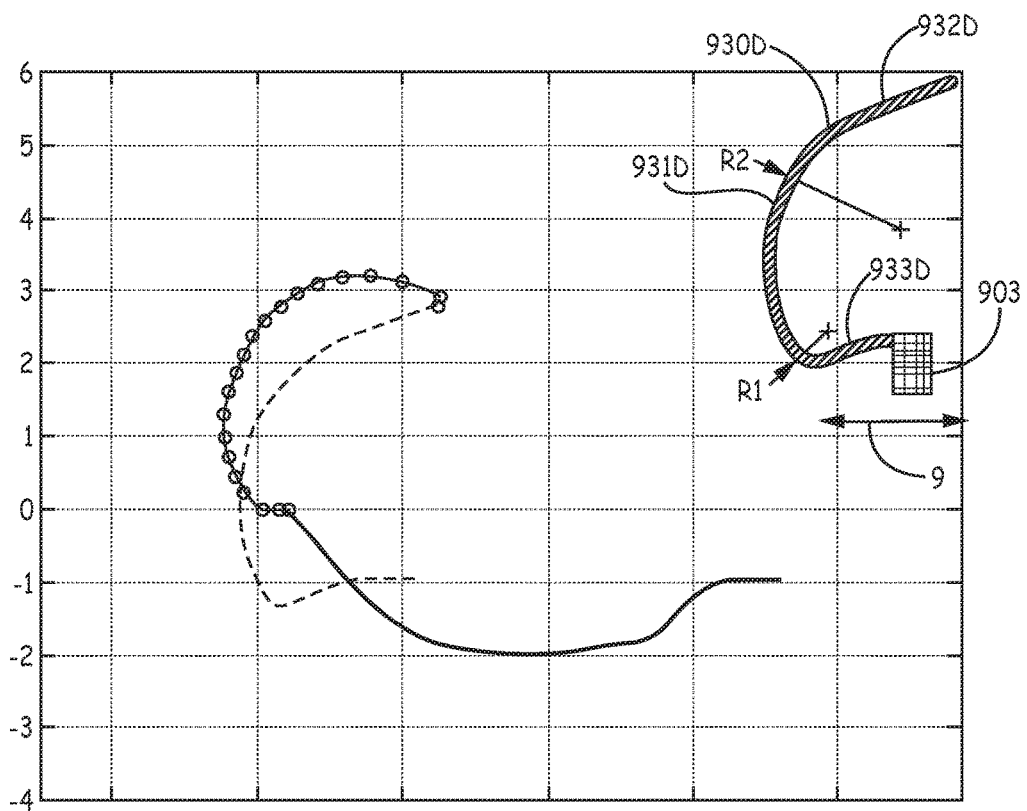

With further reference to FIGS. 9B-C, each hook portion 931B, 931C is also defined by a straight section S that extends between radii R1, R2. With further reference to the solid lines in the plots of FIGS. 9A-D, it may be seen how straight sections S can somewhat flatten the opened profile of tine portions 930B, 930C. Finally, in comparing the segmented lines of the FIG. 9A-D plots, which correspond to the estimated tissue penetration path of each of tine portions 930A-D, to that in the FIG. 5 plot for tine portion 230, it can be appreciated that the relatively shorter lengths of distal segments 932A-D, in combination with the corresponding profiles of tine portions 930A-D, lead to a reduction in tissue volume that is potentially compressed by each of the penetrated tine portions 930A-D during subsequent relaxation toward the pre-set curvature (dashed lines).

Because a reduction in the length, and/or tapering for strain relief of tine portions, can, in some instances, hinder initial tine penetration upon deployment (e.g., according to the method described above in conjunction with FIGS. 3B-C), additional embodiments of the present invention, which are described below in conjunction with FIGS. 10A-C and FIGS. 11A-B, include tissue-piercing distal tips that are configured to enhance initial tine penetration. With reference to FIGS. 3A-B, the initial penetration of tine portions 230 rely upon a stiffness of tine portions 230 being greater than that of tissue T, and upon an orientation of tissue-piercing tip 322 relative to tissue T, when device 200 is loaded in catheter distal end 310, with hook segments 31 elastically deformed into the open position.

Figure 1:
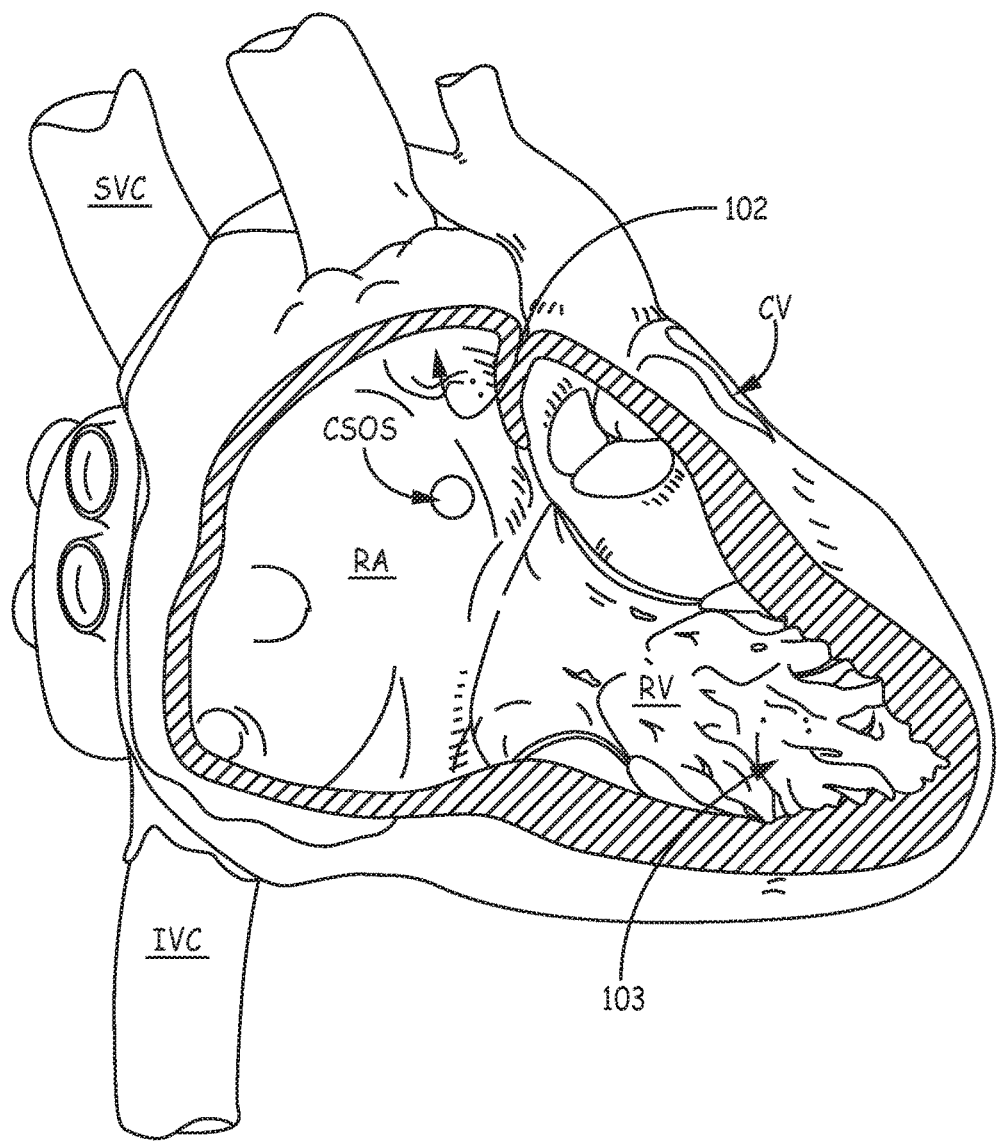
FIG. 1 is a schematic diagram showing potential implant sites for embodiments of the present invention.
Figure 10A:
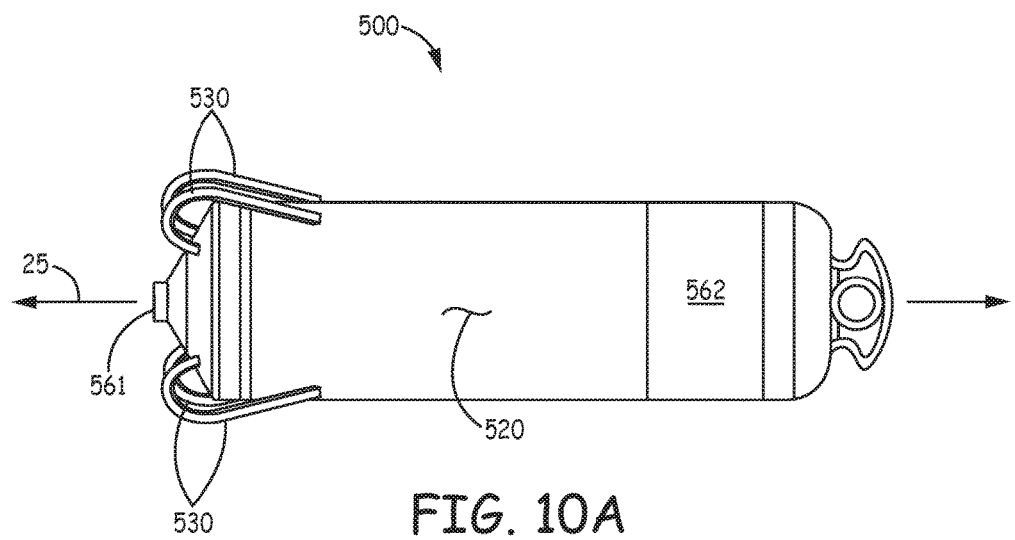
FIG. 10A is a plan view of an implantable medical device, according to some alternate embodiments of the present invention.

FIG. 10A is a plan view of an implantable medical device 500, according to some embodiments of the present invention. FIG. 10A illustrates device 500 including a hermitically sealed housing 520 and a pair of electrodes 561, 562; housing 520, like housing 220 of device 200, contains control electronics and a power source (not shown), which, for example, coupled with electrodes 561, 562, are adapted for cardiac pacing and sensing. FIG. 10A further illustrates device 500 including tine portions 530, which are adapted to penetrate tissue in order to secure device 500 at an implant site, for example, a cardiac site in the right atrium RA or the right ventricle RV (FIG. 1).

Figure 10B:
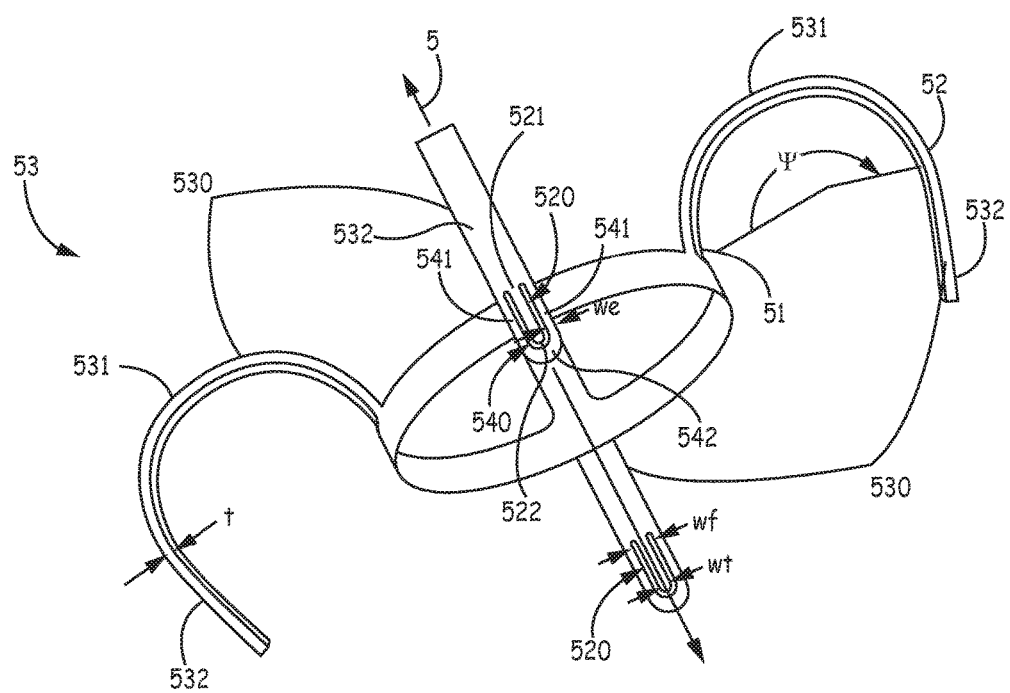
FIG. 10B is a perspective view of a tissue-penetrating fixation component, according to some embodiments, separated from the device of FIG. 10A.

FIG. 10B is a perspective view of a tissue-penetrating fixation component 53, according to some embodiments of the present invention, which is shown separated from device 500, and which includes tine portions 530. FIG. 10B illustrates component 53 also including a base portion 503, from which tine portions 530 extend. According to the illustrated embodiment, base portion 503 of fixation component 53 defines a longitudinal axis 5 of component 53 and is configured for attachment to device 500 so that axis 5 is approximately aligned with a longitudinal axis 25 of device 500. Component 53 may be part of a subassembly that forms a distal end of device 500, and which also includes electrode 561, for example, like the aforementioned subassembly that is disclosed in the above referenced and incorporated by reference passages of the detailed description of commonly-assigned U.S. patent application '690.

FIG. 10B further illustrates each tine portion 530 of tissue-penetrating fixation component 53 including a hook segment 531 and a distal segment 532. Each hook segment 531 is shown extending along a curvature that encloses an angle ψ, from a proximal end 51 thereof to a distal end 52 thereof; and each distal segment 532 is shown extending along a relatively straight line that is approximately tangent to distal end 52 of hook segment 531. Each distal segment 532 is shown extending toward axis 5, and, according to an exemplary embodiment, angle ψ is approximately 200 degrees. According to some preferred embodiments, component 53 is manufactured by, first, laser cutting base portion 503 and tine portions 530, together, from a tube of superelastic and biocompatible metal (e.g., Nitinol), and then wrapping and holding each tine portion 530 about a mandrel for a heat setting process that pre-sets the illustrated curvature of each hook segment 531. As mentioned above, manufacturing methods such as these are known to those skilled in the art of forming Nitinol components. Although FIG. 10B shows base portion 503 of component 53 formed as a ring, wherein tine portions 530 are integrally formed therewith, and spaced apart from one another about a perimeter of the ring, in alternate embodiments of tissue penetrating fixation components, one or more tine portions may be formed individually and then attached to a base portion that is configured in any suitable fashion for attachment to device 500.

In order to provide more flexibility in selecting a suitable implant location for device 500, a length of distal segment 632 of each tine portion 630 is relatively short compared to that of distal segment 232 of tine portion 230, for example, between approximately 0.05 inch and approximately 0.1 inch. The shorter length can help to prevent perforation through the wall of a structure, for example, the heart, at some implant locations, and can reduce a probability for penetrated tine portions 530 to interfere with blood vessels, which interference, for example, may compromise coronary blood supply, as described above. However, with reference back to FIGS. 3A-C, after device 500 is loaded in distal end 310 of catheter 300, and opening 313 of distal end 310 is positioned in proximity to tissue at a potential implant site, the reduced length of tine portions 530 may hinder initial tine penetration. A sharper terminal end of distal segment 532 can solve this problem but may lead to tissue tearing, upon insertion and/or retraction; thus a relatively blunt terminal end of distal segment 532 is preferred. So, with further reference to FIG. 10B, each distal segment 532 includes a tooth 520 and a relatively blunt end 540, which surrounds tooth 520.

FIG. 10B illustrates end 540 including a pair of legs 541 and a distal arch 542 that extends between legs 541, distal to tip 522 of tooth 520, for example, being spaced apart therefrom by approximately 0.005 inch. Each tooth 520 has a length, which is defined from a foot 521 thereof to a tissue-piercing tip 522 thereof, for example, being between approximately 0.025 inch and approximately 0.045 inch, and legs 541 extend along the length of tooth 520, on opposing sides thereof. Each tooth 520 and corresponding end 540 may be laser cut at the same time that tine portions 530 and base portion 503 are cut from the aforementioned tube.

Figure 10C:
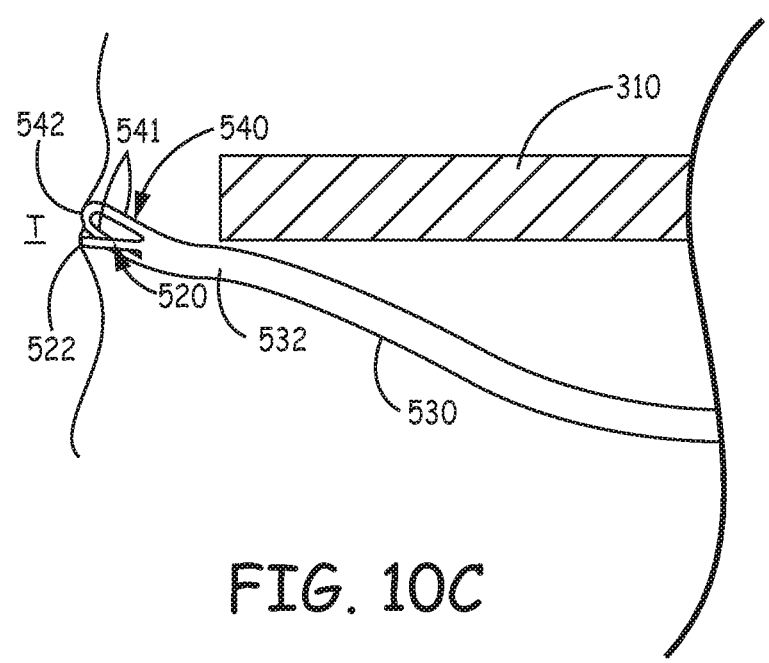
FIG. 10C is an enlarged detail view of a distal segment of one of the tine portions of the FIG. 10B component initially contacting tissue at an implant site.

According to the illustrated embodiment, legs 541 of end 540 are configured to bend in elastic deformation when distal arch 542 is pushed against tissue at a potential implant site, for example, as illustrated in FIG. 10C, so that tip 522 of tooth 520, which is configured to resist bending, is exposed to pierce the tissue. FIG. 10C is an enlarged detail view of distal segment 532 as tine portion 530 is pushed into contact with tissue T at the implant site. With reference back to FIGS. 3A-B, it should be understood that pushing distal arch 542 against the tissue T may be accomplished, as described above for device 200, after device 500 is loaded into distal end 310 of catheter 300 so that hook segments 531 of tine portions 530 are elastically deformed into the open position, at which distal segments 532 are directed distally toward opening 313 of distal end 310. After tip 522 of each tooth 520 has pierced the tissue, in response to the relatively high push force for initial deployment, legs 541 of end 540 can relax back into line with tooth 520 so that distal arch 542, upon subsequent penetration/insertion of tine portions 530 into tissue, and upon retraction thereof from the tissue, if necessary, prevents tip 522 from tearing the tissue. With reference back to FIG. 10B, according to an exemplary embodiment, a thickness t of each tine portion 530, which is relatively constant along the entire length thereof, is approximately 0.005 inch, a width wf of foot 521 of tooth 520 is between approximately 0.010 inch and approximately 0.015 inch, a width wt of tip 522 of tooth 520 is approximately 0.003 inch, and a width we of legs 541 and distal arch 542 is approximately 0.005 inch.

FIG. 11A is an elevation view of a tissue-penetrating fixation component 83, according to some alternate embodiments of the present invention, which may also be incorporated in the exemplary device of FIG. 10A. FIG. 11A illustrates component 83 including a base portion 803 and a plurality of tine portions 830 extending therefrom, similar to component 53, wherein each tine portion 830 includes a hook segment 831 and a distal segment 832 that are configured to address both of the aforementioned issues related to tissue penetration and fatigue life. Component 83 may be cut and formed from a Nitinol tube in a manner similar to that described above for component 53. FIG. 10A further illustrates each hook segment 831 being pre-set to extend along a curvature that encloses angle φ, from a proximal end 81 thereof to a distal end 82 thereof; and each distal segment 832 is shown extending along a relatively straight line that is approximately tangent to distal end 82 of hook segment 831. According to the illustrated embodiment, angle γ is approximately 180 degrees, so that each distal segment 832 extends approximately parallel to a longitudinal axis 8 of component 83. The pre-set curvature of hook segment 831 is defined by a single radius R, which may be approximately 0.085 inch.

FIG. 11B is a plan view of tine portion 830, prior to forming the pre-set curvature thereof. FIGS. 11A-B illustrate each tine portion 830 including a tapered hook portion 831, similar to hook portions 631, 731 of tine portions 630, 730, described above, wherein second width W2, in proximity to distal end 82 of hook segment 831, is less than first width W1, in proximity to a proximal end 81 of hook segment 831. FIGS. 11A-B further illustrate distal segment 832 having a width W3 that is greater than the second width W2. Distal segment 832, like distal segment 532 of component 53, includes tooth 520 and end 540 to facilitate tissue piercing without tearing, as described above. Like component 53, a thickness t of each tine portion 830, which is relatively constant along the entire length thereof, may be approximately 0.005 inch, and distal segment 832 thereof may conform to the aforementioned exemplary dimensions of tooth 520 and end 540.

In the foregoing detailed description, the invention has been described with reference to specific embodiments. However, it may be appreciated that various modifications and changes can be made without departing from the scope of the invention as set forth in the appended claims.

What is claimed is:

1. A fixation component for an implantable medical device, the fixation component comprising:
   a base portion; and
   a plurality of tines that extend from the base portion, wherein each tine of the plurality of tines is elastically deformable between a pre-set position and an open position, and wherein each tine of the plurality of tines comprises a hook segment that, when positioned in the pre-set position, extends along a pre-set curvature, wherein the pre-set curvature is defined by at least a first radius and a second radius distal to the first radius, wherein the first radius is different than the second radius, and wherein the first radius and the second radius are nonzero.

2. The fixation component of claim 1, wherein each tine of the plurality of tines further comprises a straight distal segment terminated by a tip, the straight distal segment distal of the hook segment.

3. The fixation component of claim 1, wherein the first radius and the second radius extend in the same direction.

4. The fixation component of claim 1, wherein the first radius is less than the second radius.

5. The fixation component of claim 1, wherein the first radius is within a range from about 0.25 millimeters (mm) to about 1.04 mm, and wherein the second radius is within a range from about 1.65 mm to about 2.4 mm.

6. The fixation component of claim 1, wherein the hook segment comprises at least one straight section extending between the first radius and the second radius.

7. The fixation component of claim 6, wherein the at least one straight section is configured to flatten a profile of the open position of the at least one tine.

8. The fixation component of claim 1, wherein the hook segment comprises a taper.

9. The fixation component of claim 1, wherein the pre-set curvature is configured to reduce a tissue volume that is compressed by the at least one tine in the pre-set position.

10. An implantable medical device (IMD) comprising:
    a hermetically sealed housing, the housing containing control electronics and a power source of the device and defining a longitudinal axis of the device; and
    a fixation component coupled to the hermetically sealed housing, the fixation component comprising:
       a base portion; and
       a plurality of tines that extend from the base portion, wherein each tine of the plurality of tines is elastically deformable between a pre-set position and an open position, and wherein each tine of the plurality of tines comprises a hook segment that, when positioned in the pre-set position, extends along a pre-set curvature, wherein the pre-set curvature is defined by at least a first radius and a second radius distal to the first radius, wherein the first radius is different than the second radius, and wherein the first radius and the second radius are nonzero.

11. The IMD of claim 10, wherein the at least one tine further comprises a straight distal segment terminated by a tip, the straight distal segment distal of the hook segment.

12. The fixation component of claim 11, wherein the straight distal segment is less than about 2.54 mm.

13. The IMD of claim 10, wherein the first radius and the second radius extend in the same direction.

14. The fixation component of claim 10, wherein the first radius is less than the second radius.

15. The fixation component of claim 10, wherein the first radius is within a range from about 0.25 millimeters (mm) to about 1.04 mm, and wherein the second radius is within a range from about 1.65 mm to about 2.4 mm.

16. The IMD of claim 10, wherein the hook segment comprises at least one straight section extending between the first radius and the second radius.

17. The IMD of claim 16, wherein the at least one straight section is configured to flatten a profile of the open position of the at least one tine.

18. The IMD of claim 10, wherein the pre-set curvature is configured to reduce a tissue volume that is compressed by the at least one tine in the pre-set position.

19. A medical device system, comprising:
    an implantable medical device (IMD) comprising a hermetically sealed housing and a fixation component coupled to the hermetically sealed housing, the fixation component comprising:
       a base portion; and
       a plurality of tines that extend from the base portion, wherein each tine of the plurality of tines is elastically deformable between a pre-set position and an opened position, and wherein each tine of the plurality of tines comprises:
          a hook segment that, when positioned in the pre-set position, extends along a pre-set curvature, wherein the pre-set curvature is defined by a first radius and a second radius distal to the first radius, wherein the first radius is different than the second radius, and wherein the first radius and the second radius are nonzero; and
          a straight distal segment terminated by a tip, the straight distal segment distal of the hook segment; and
    a delivery catheter extending from a proximal end to a distal end having a distal opening defined by a wall configured to contain the IMB, wherein the straight distal segment, when positioned in the opened position inside the distal end, is oriented at an acute angle relative to the wall.

20. The medical device system of claim 19, wherein the first radius is within a range from about 0.25 millimeters (mm) to about 1.04 mm, and wherein the second radius is within a range from about 1.65 mm to about 2.4 mm.

* * * * *